United States Patent [19]

Okada et al.

[11] Patent Number: 5,354,518

[45] Date of Patent: Oct. 11, 1994

[54] METHOD FOR MANUFACTURING A FIBERSCOPIC CATHETER

[75] Inventors: Yosuke Okada; Yumiko Suzuki, both of Shizuoka, Japan

[73] Assignee: Sherwood Medical Company, St. Louis, Mo.

[21] Appl. No.: 16,924

[22] Filed: Feb. 11, 1993

[51] Int. Cl.$^5$ ............................................. B29C 61/08
[52] U.S. Cl. ............................... 264/1.25; 128/4; 264/516; 264/573; 264/230; 264/342 R; 264/DIG. 71; 264/1.28
[58] Field of Search ........... 264/230, 342 R, DIG. 71, 264/573, 1.5, 572, 516, 530, 532; 128/4; 156/86

[56] References Cited

U.S. PATENT DOCUMENTS

| | | | |
|---|---|---|---|
| 3,861,972 | 1/1975 | Glover et al. | 264/DIG. 71 |
| 4,100,246 | 7/1978 | Frisch | 264/230 |
| 4,173,392 | 11/1979 | Ekinaka et al. | 264/1.5 |
| 4,227,293 | 10/1980 | Taylor | 29/447 |
| 4,411,055 | 10/1983 | Simpson et al. | 264/573 |
| 4,495,134 | 1/1985 | Ouchi et al. | 264/573 |
| 4,593,973 | 6/1986 | Yoshida et al. | 350/96.29 |
| 4,723,936 | 2/1988 | Buchbinder et al. | 604/95 |
| 4,782,819 | 11/1988 | Adair | 128/6 |
| 4,813,400 | 3/1989 | Washizuka et al. | 128/6 |
| 4,878,492 | 11/1989 | Sinofsky et al. | 128/303.1 |
| 4,927,222 | 5/1990 | Kamiya et al. | 350/96.15 |
| 5,041,089 | 8/1991 | Mueller et al. | 604/96 |
| 5,061,273 | 10/1991 | Yock | 606/194 |
| 5,108,525 | 4/1992 | Gharibadeh | 264/230 |
| 5,116,317 | 5/1992 | Carson, Jr. et al. | 128/6 |
| 5,152,277 | 10/1992 | Honda et al. | 128/4 |
| 5,169,568 | 12/1992 | Ainger, III | 264/1.5 |
| 5,221,387 | 6/1993 | Robbins et al. | 264/DIG. 71 |

FOREIGN PATENT DOCUMENTS

| | | | |
|---|---|---|---|
| 3425649 | 1/1986 | Fed. Rep. of Germany | 264/1.5 |
| 56-25412 | 3/1981 | Japan | 264/572 |
| 2-95811 | 4/1990 | Japan | 264/1.5 |

*Primary Examiner*—Jeffery Thurlow
*Attorney, Agent, or Firm*—Andrew J. Beck; Montgomery W. Smith; David A. Warmbold

[57] ABSTRACT

A method of manufacture of a fiberscopic catheter having a tightly fitted optical glass fiber bundle received within an internal lumen of the catheter. The lumen for receiving the optical glass fiber bundle is heated and expanded under internal fluid pressure. The catheter and lumen are then cooled with the lumen still under the internal fluid pressure. After cooling, the fluid pressure is released and the lumen retains its expanded condition. An optical glass fiber bundle is inserted into the expanded lumen to a predetermined position within the catheter. The catheter and lumen are reheated to contract the expanded diameter of the lumen about the optical glass fiber bundle to provide a fiberscopic catheter having a tightly fitted fiber optic bundle within the catheter.

12 Claims, 5 Drawing Sheets

METHOD FOR MANUFACTURING A FIBERSCOPIC CATHETER

BACKGROUND OF THE INVENTION

1. Field of the Invention

The present invention pertains to a method for manufacturing a fiberscopic catheter, which is also called an endoscopic catheter, and which is used in the endoscopic viewing of relatively slender tubes in the body such as blood vessels.

2. Description of the Prior Art

An example of conventional fiberscopic catheters are disclosed in Tokkai (Patent Disclosure) Sho 63 (1988)-119732. The fiberscopic catheter is equipped with an optical glass fiber bundle and the catheter is inserted in the body of a patient just like a regular catheter. Obviously, it is desirable for the catheter to be as slender as possible to minimize pains and injuries to the patient during its insertion. Also, a more slender catheter improves its usefulness in facilitating endoscopic observation of blood vessels or fine tube lumens.

Accordingly, various attempts have been made to reduce the outer diameter of the fiberscopic catheter without downgrading the quality of the images it produces. Such attempts include making finer optical glass fibers and making the fiberscopic catheter more compact by fusing the body of the catheter to the optical glass fiber bundle.

In addition, methods for improving the range of view by blocking the blood flow to provide an unobstructed view from the end of the fiberscopic catheter have been attempted. In this method, a multi-tubed fiberscopic catheter is utilized in which a balloon portion is included at the tip of the fiberscopic catheter. In particular, after the catheter's tip is inserted to the prescribed position in a blood vessel, the balloon portion is expanded to block the blood flow. An example of such a multi-tubed fiberscopic catheter was reported in MEBIO, Medical View, Inc., September 1990, pp. 107-114.

As described above, the conventional method for inserting and tightening an optical glass fiber bundle in the specified lumen of a fiberscopic catheter requires that the diameter of the lumen be greater than the diameter of the optical glass fiber bundle. However, such a method of manufacture generally results in a fiberscopic catheter having a large gap between the outer diameter of the optical glass fiber bundle and the inner wall of the catheter lumen. A fiberscopic catheter having such a large gap between the optical glass fiber bundle and the inner wall of the catheter will mean that the catheter's outer diameter will be unnecessarily large. This contradicts the demand for minimizing the overall diameter of the catheter for ease of insertion into a patient's blood vessel.

SUMMARY OF THE INVENTION

An object of the present invention is to provide a method for manufacturing a fiberscopic catheter which resolves such problems as those described above by minimizing any gaps in the interior of the catheter so that the outer diameter of the catheter can be made as small as possible without downgrading the quality of the image.

The method for manufacturing the fiberscopic catheter of the present invention consists of the following steps: expanding and deforming the catheter's lumen such that the lumen is heated and expanded under fluid pressures; cooling the catheter while the lumen is in the pressurized state to a predetermined temperature, and then releasing the pressure; inserting an optical glass fiber bundle into the expanded lumen; and contracting the lumen by reheating the catheter after the insertion of the fiber bundle to contract the catheter's body tightly about the fiber bundle.

In a second manufacturing method, the said expansion and deformation step includes inserting the catheter in a cylinder made of a material with high rigidity at an elevated temperature and having an inner diameter greater by a prescribed dimension than the outer diameter of the catheter to limit expansion and deformation of the catheter's body.

A third manufacturing method for a multi-tubed catheter having multiple lumens includes a step preceding the said expansion and deformation step in which a rod with a prescribed or predetermined cross section is inserted into at least one of the lumens of the catheter not equipped with or utilizing an optical glass fiber bundle to limit deformation of such lumens during the heating and/or reheating steps.

In the present invention, the lumen of the catheter is expanded by application of heat and a fluid pressure and is cooled while under this pressure. Consequently, the expanded deformation generated during this step is frozen in that deformed or enlarged state. An optical glass fiber bundle is then inserted in the expanded lumen, The catheter is then reheated such that the frozen expanded deformation is released by the thermal contraction of the tube and the catheter regains most of its original dimensions. The optical glass fiber bundle is now withheld within the lumen in a lightly tightened state.

In the second manufacturing method, the catheter is first inserted in a highly rigid cylinder before the expanding and deforming step and, consequently, the outer diameter of the expanded catheter is restricted so that it does not exceed the inner diameter of the cylinder.

In the third manufacturing method involving multi-tubed catheters, rods are inserted into the lumens which are not to be expanded before the expanding and deforming step. This would prevent these lumens from being totally or partially closed during the expanding and deforming step.

BRIEF DESCRIPTION OF THE DRAWINGS

Other features of the invention will be apparent from the following description of the embodiments shown, by way of example, in the accompanying drawings briefly described hereafter.

DETAILED DESCRIPTION OF THE INVENTION

Figure 1A:
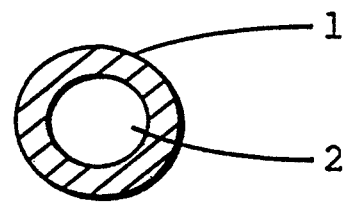
FIGS. 1(a)–1(d) illustrate the steps utilized in one method for manufacturing a single-tubed fiberscopic catheter with the catheter shown in cross-section.

In accordance with the present invention a method is disclosed for manufacturing single-tubed or multi-tubed fiberscopic catheters. The method of manufacture provides such a catheter wherein the catheter body is snugly received about the fiber optic cable or bundle so as to minimize the overall outside diameter of the fiberscopic catheter. The present invention will now be described in detail by way of the embodiments shown in the drawings and discussed below.

For the first embodiment, shown in FIGS. 1(a)–1(d), a method is described for manufacturing a single-tubed fiberscopic catheter. Here, a single-tube refers to a fiberscopic catheter which has an optical glass fiber bundle inserted in a single lumen of the catheter tube.

FIGS. 1(a)–1(d) provide a cross-sectional illustration of the manufacturing steps for the single-tubed fiberscopic catheter in a first embodiment of the present invention. The various steps are explained in each FIG. 1(a) through 1(d).

In FIG. 1(a), the single-tubed catheter 1 made of PVC (polyvinylchloride) containing 40% plasticizer is placed in an air-heating furnace (not shown in the figure) and heated to 80° C. for 5 minutes. The catheter 1 has original dimensions before expansion or deformation of an outer diameter of 2.2 mm and an inner diameter of 1.5 mm. This hollow space within the inner diameter 1.5 mm constitutes the lumen 2.

Figure 1B:
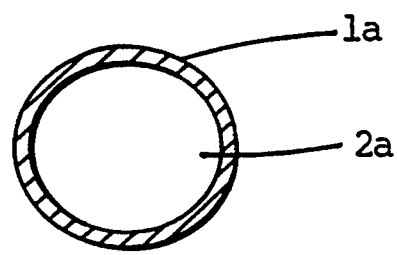

In FIG. 1(b), the lumen 2 is then pressurized to two (2) atmospheres for 5 minutes in the heated state described in FIG. 1(a). The catheter is removed from the air-heating furnace under the pressurized condition and is left for 10 minutes to be allowed to cool to room temperature. After cooling, the pressure is released from the catheter 1a which retains its expanded shape (with some deformation). The lumen 2a has also been expanded and the catheter now has an outer diameter of about 2.7 mm and an inner diameter of about 2.3 mm.

Figure 1C:
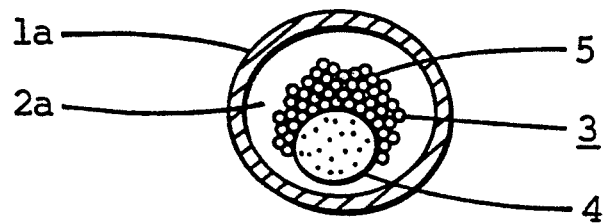

In FIG. 1(c), an optical glass fiber bundle 3 is shown inserted in the expanded lumen 2a to the prescribed position within the catheter. The optical glass fiber bundle 3 includes a lighting guide 5 which is attached in a crescent shape around an imaging guide 4 which are both bundled together in the form of a round rod. The structure and function of the imaging guide 4 and the lighting guide 5 in a fiberscopic catheter are commonly known, the description herein of which is therefore omitted.

Figure 1D:
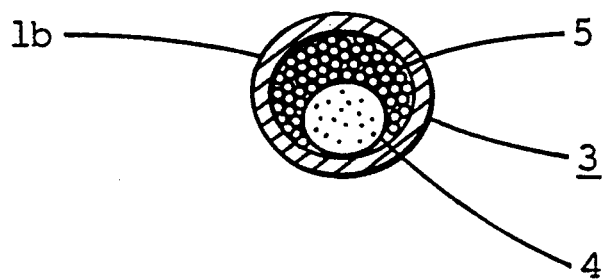

When the catheter 1a as shown in FIG. 1(c) is placed in the air-heating furnace again and heated at 100° C. for 10 minutes under atmospheric pressure, the catheter 1a contracts to an outer diameter of about 2.3 mm and an inner diameter of about 1.6 mm, to obtain the contracted catheter 1b as shown in FIG. 1(d). The optical glass fiber bundle 3 is protected by the contracted catheter 1b and no hollow or vacant space in the lumen 2 of the single-tubed fiberscopic catheter is formed.

Figure 2:
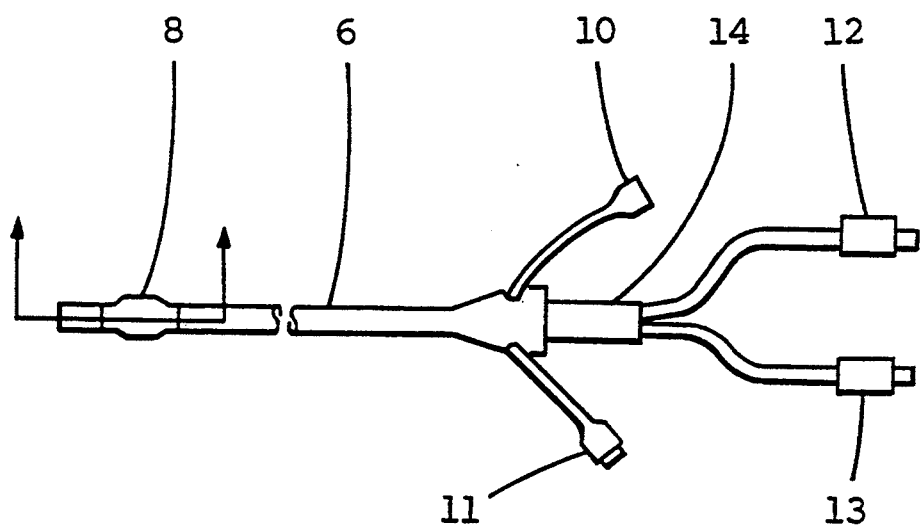
FIG. 2 is a schematic top view of a multi-tubed fiberscopic catheter which can be manufactured in accordance with another method of the present invention.
Figure 3:
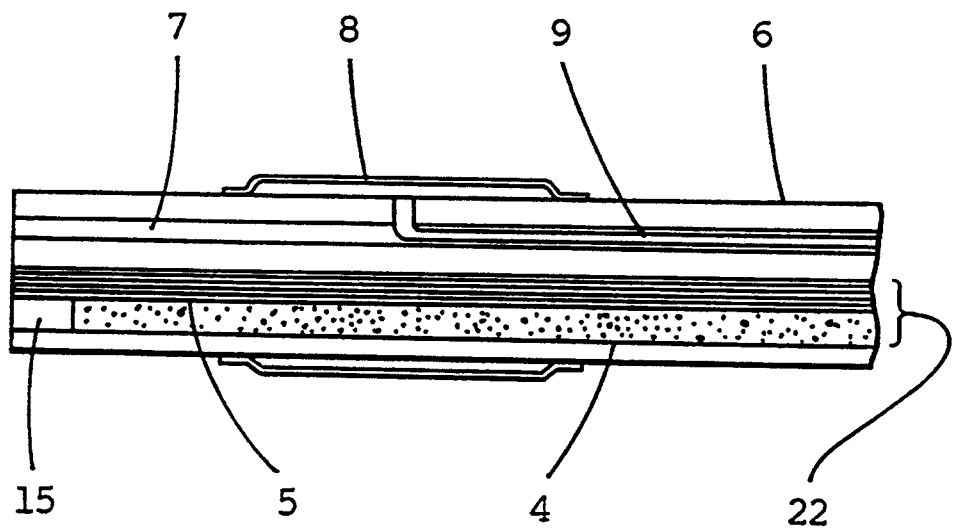
FIG. 3 is an enlarged view of a longitudinal section of the catheter end portion taken along the line 3—3 of FIG. 2 depicting the balloon of the present invention.

In the second embodiment of the present invention, shown in FIGS. 2 through 4, a method for manufacturing a multi-tubed fiberscopic catheter is disclosed. A multi-tube fiberscopic catheter refers to a catheter which has a principal lumen for the optical glass fiber bundle as well as various auxiliary lumens such as a balloon expanding lumen for injecting expanding fluid into a balloon contained near the catheter's distal end and various other lumens for providing additional functions at the distal tip of the catheter, as illustrated by the endoscopic catheter with balloon shown in FIGS. 2 and 3.

FIG. 2 shows such a multi-tubed fiberscopic catheter and FIG. 3 shows an enlarged longitudinal section of the catheter end portion of FIG. 2 containing the expanding balloon portion.

As seen from the multi-tubed catheter shown in FIGS. 2 and 3, the triple-tubed catheter 6 consists of the principal lumen 22 which includes an optical glass fiber bundle made up of an imaging guide 4 and a lighting guide 5. The catheter 6 further includes secondary lumens such as a flash lumen 7 and a balloon lumen 9 for expanding the balloon 8 by fluid (air or liquid). To accommodate these components, the principal lumen 22 is placed at a position deviated from the center of the catheter 6, and the flash lumen 7 and the balloon lumen 8 are formed in the thick walled portion generated by this deviation. An objective rod lens 15 is installed at the tip of the imaging guide 4. A connector 10 is provided for the flash lumen 7 which connects the flash lumen 7 with the flash device (not shown). A connector 11 is provided for expansion of the balloon which connects the balloon lumen 9 with the balloon expanding device (not shown). A cover tube 14 includes a lighting guide connector 12 and an imaging guide connector 13.

In an alternate embodiment of the present invention, FIGS. 4(a) through 4(d) provide a cross-sectional illustration of the manufacturing steps for the multi-tubed fiberscopic catheter. FIGS. 5(a) through 5(c) are the schematic cross-sectional illustration of the changes in dimensions and geometry of the catheter corresponding to various heat treatments of this process. The various steps are explained below for each FIG. 4(a) through FIG. 4(d).

Figure 4A:
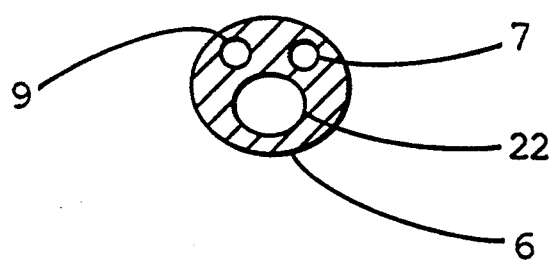
FIGS. 4(a)–4(d) illustrate the steps utilized in a method for manufacturing a multi-tubed fiberscope catheter with the catheter shown in cross-section.
Figure 5A:
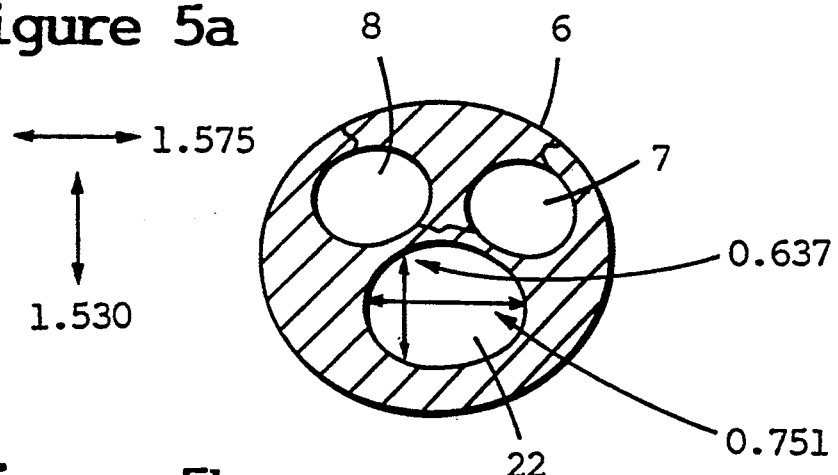
FIGS. 5(a)–5(c) are schematic cross-sectional views of the changes in dimensions and geometry of the catheter corresponding to various heat treatments during the manufacturing steps illustrated in FIGS. 4(a)–4(d).
Figure 5B:
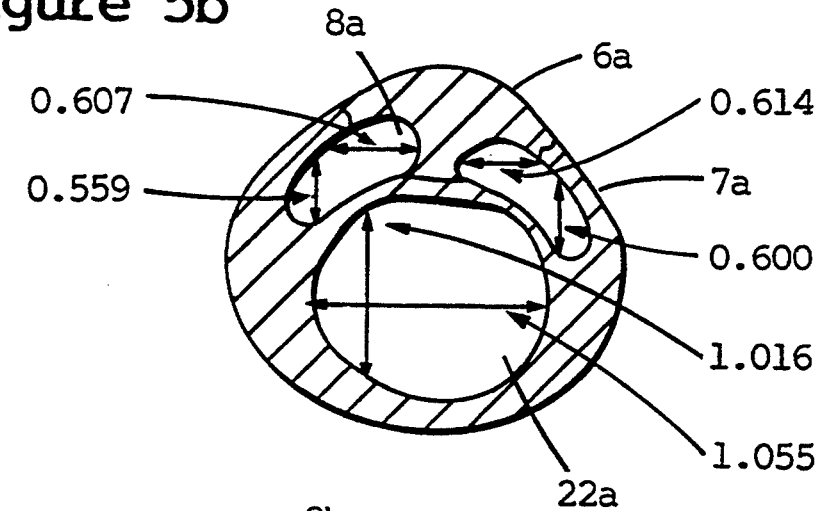
Figure 5C:
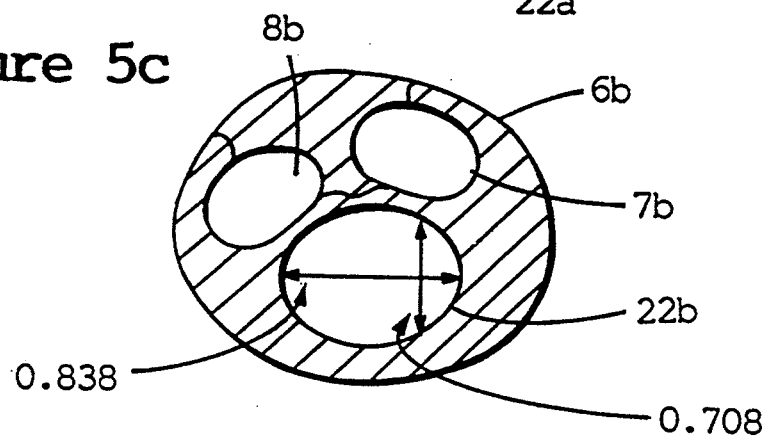

In FIG. 4(a), a triple-tubed catheter 6 made of PVC containing 55% plasticizer is placed in an air-heating furnace heated to 80° C. for 5 minutes. The original dimensions of the catheter 6 are a nearly circular cross-section having a vertical outer diameter of 1.530 mm and a horizontal outer diameter of 1.575 mm, as shown in FIG. 5(a). The principal or main lumen 22 which receives an optical glass fiber bundle 3 has vertical and horizontal outer diameters of 0.637 mm and 0.751 mm, respectively.

Figure 4B:
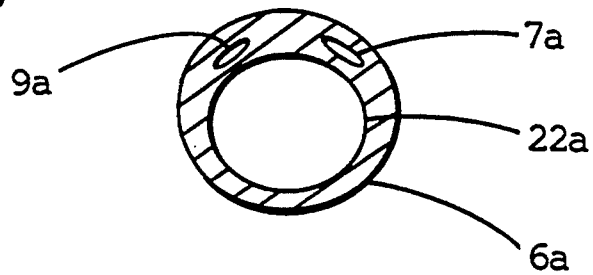

In FIG. 4(b), the lumen 22 is pressurized to 2 atmospheres for 10 minutes at 80° C. The catheter is removed from the air-heating furnace under a pressurized condition and is cooled to room temperature. When the pressure is released from the catheter after cooling, the lumen 22 is expanded to provide an expanded catheter 6a having an expanded lumen 22a as shown in FIG. 4(b). However, since the flash lumen 7 and the balloon lumen 9 are not pressurized, they result in somewhat flattened lumens (i.e., a deformed flash lumen 7a and a deformed balloon lumen 9a) as shown in FIG. 4(b). The catheter's shape is more accurately shown in FIG. 5(b). The expanded lumen 22a has a vertical diameter of about 1.055 mm and a horizontal diameter of about 1.016 mm. This expansion amounts to an enlargement of about 1.5 times the catheter's original dimensions.

Figure 4C:
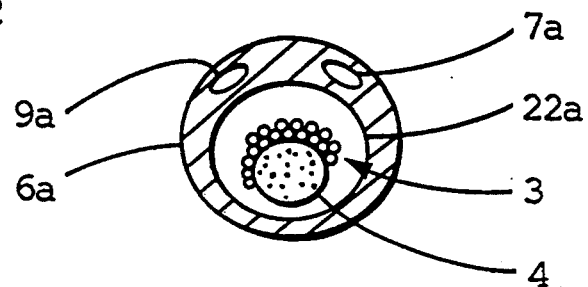

In FIG. 4(c), the optical glass fiber bundle 3 is shown inserted into the expanded lumen 22a to the prescribed position within catheter 6a.

Figure 4D:
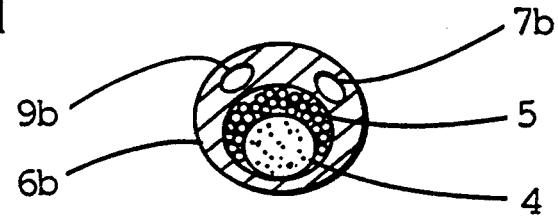

In FIG. 4(d), the catheter is shown after again being placed in the air-heating furnace and heated at 100° C. for 10 minutes under atmospheric pressure. The expanded catheter 6a contracts by 30-40% and returns the catheter to the contracted shape shown at 6b in FIG. 4(d). The lumen 22b of the contracted catheter 6b has vertical and horizontal inner diameters of 0.705 mm and 0.838 mm, respectively, and the flash lumen 7b and the balloon lumen 9b have a recovered shape as shown in FIG. 5(c). The optical glass fiber bundle 3 in the contracted lumen 22b is thus shielded within the contracted catheter 6b such that a multi-tubed fiberscopic catheter of the present invention is formed.

Figure 6A:
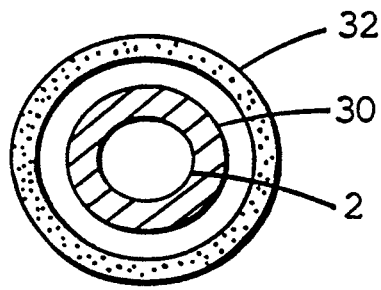
FIGS. 6(a) and 6(b) illustrate an alternative embodiment for the method for manufacturing a single-tubed fiberscopic catheter shown in FIG. 1.
Figure 6B:
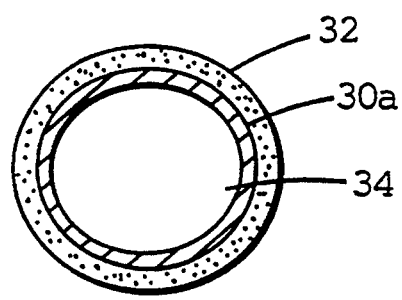

In a third embodiment of the present invention, shown in FIGS. 6(a) and 6(b), an alternate embodiment of the steps for manufacturing the single-tubed fiberscopic catheter of the first embodiment shown in FIG. 1 is provided. As shown in FIG. 6(a), a catheter 30 is inserted into a cylinder 32 having an inner diameter which his slightly smaller than the outer diameter of the expanded catheter 30a shown in FIG. 6(b). In this embodiment, it is preferable to use for the cylinder 32, a pipe with sufficiently large rigidity at elevated temperatures, (e.g., a metallic pipe). When the catheter in the state shown in FIG. 6(a) is expanded by heating, as discussed earlier in reference to FIGS. 1(a) and 1(b), a catheter having an expanded lumen 34 is obtained. The outer diameter of the expand catheter 30a is restricted by the inner diameter of the cylinder 32. Therefore, this method has an advantage in that it yields, even with some operational errors with respect to pressurization, an expanded catheter 30a having outer diameters within controllable dimensional tolerances.

As discussed previously in the first embodiment and FIG. 1(a)-1(d), the fiberoptic bundle 3 can be inserted into the expanded lumen 34 and the expanded catheter 30a cooled until the catheter contracts about the fiber optic bundle 3. The cylinder 32 is removed from about the catheter 30 and a single-tube fiberscopic catheter similar in appearance to FIG. 1(d) is formed. Also, needless to say, the manufacturing step discussed here using cylinder 32 can be applied to the manufacturing method discussed in the second embodiment referring to a multi-tubed fiberscopic catheter as shown in FIGS. 4(a)-4(d) and FIGS. 5(a)-5(c).

Figure 7A:
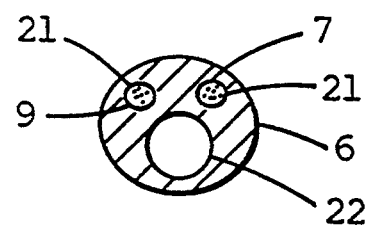
FIGS. 7(a) and 7(b) illustrate an alternative embodiment for the method of manufacturing a multi-tubed fiberscopic catheter shown in FIG. 4.
Figure 7B:
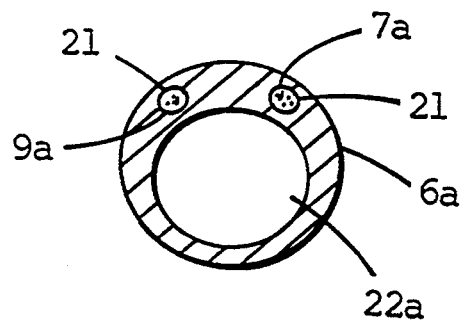

In a further embodiment, shown in FIGS. 7(a)-7(b) an alternate embodiment of the steps for manufacturing the multi-tubed fiberscopic catheter of embodiment 2 (shown in FIGS. 4(a)-4(d)). Before the heat expansion of the lumen 22, as described in the steps of FIGS. 4(a) and 4(b), rods 21 are inserted in the auxiliary or alternate lumens such as the flash lumen 7 and the balloon lumen 9, as shown in FIG. 7(a). Rods 21 should have a high rigidity at elevated temperatures. When the aforementioned heat expansion step is performed on a catheter shown in FIG. 7(a), the rods 21 remain undeformed in the somewhat deformed flash lumen 7a and the balloon lumen 9a, as shown in FIG. 7(b). If the rods are removed after the cooling step discussed in relation to FIG. 4(d), then the subsequent steps in FIG. 4 can be followed without any problem. In this embodiment, two rods 21 are used. However, if desired, only one rod 21 can be used just for the balloon lumen 9a. The method disclosed in this embodiment prevents a part of or the entire deformed balloon lumen 9a from collapsing and becoming unusable during the manufacturing process of the fiberscopic catheter.

Various embodiments of the manufacturing method of the present invention are illustrated by embodiments 1 through 4 are shown in FIGS. 1-7. Needless to say, the dimensions, the number of lumens, etc., the processing temperature and other conditions are not limited to those described in these embodiments.

Procedure

As described above, the present invention uses the following steps in the method of inserting an optical glass fiber bundle into the lumen of the catheter. The lumen in a preheated catheter is expanded by pressurization. Then the catheter is cooled while the lumen is under pressure to obtain a catheter with an expanded lumen. An optical glass fiber bundle is inserted in the expanded lumen. The catheter is subsequently reheated and the catheter body as well as the lumen contract to recover substantially the original diameter of the catheter and lumen. The optical glass fiber bundle is then fitted tightly within the lumen without any hollow spaces to allow for a fiberscopic catheter having a minimal outside diameter.

In an alternate embodiment during the process of expanding the lumen by heating, the catheter is inserted in a cylinder with high rigidity so that the excessive expansion of the catheter by over pressurizing can be prevented.

In addition, in an alternate embodiment involving a multi-tubed catheter, rods can be inserted in the secondary lumens during the step of heat expansion of the principal lumen. Therefore, the secondary lumens will not collapse during such expansion step and the secondary lumens will remain usable. This method improves the quality and quantity of catheters which remain usable after completion of the manufacturing methods discussed herein.

We claim:

1. A method of making a fiberscopic catheter having an internal lumen for receiving an optical fiber bundle, comprising the steps of:

heating the catheter and lumen in a heating device to a predetermined temperature;

introducing a pressurized fluid into the catheter's lumen to expand the internal diameter of the lumen;

cooling the catheter and lumen while under pressure to maintain the expanded internal diameter of the lumen;

releasing the internal fluid pressure within the lumen of the catheter;

inserting the optical fiber bundle into the lumen of the catheter to a predetermined position; and reheating the catheter and lumen to contract the internal diameter of the lumen about the optical fiber bundle to provide a fiberscopic catheter having a tightly fitted fiber optic bundle.

2. A method of making a fiberscopic catheter having an internal lumen for receiving an optical fiber bundle, comprising the steps of:

heating the catheter and internal lumen in a heating device at about 80° C. for about 5 minutes;

pressurizing the internal lumen of the catheter to about two (2) atmospheres pressure for about 5 minutes to expand the internal diameter of the lumen and outer diameter of the catheter;

cooling the catheter and lumen while under pressure to maintain the expanded diameters of the catheter and lumen;

releasing the internal fluid pressure within the lumen of the catheter;

inserting the optical fiber bundle into the lumen of the catheter to a predetermined position within the catheter;

reheating the catheter and lumen to about 100° C. for about 10 minutes to contract the internal diameter of the lumen about the optical fiber bundle to provide a fiberscopic catheter having a tightly fitted fiber optic bundle.

3. A method as claimed in claim 1, wherein the step of expanding the internal diameter of the catheter's lumen is accomplished by heating the catheter in a heating device at about 80° C. for about 5 minutes and pressurizing the internal lumen of the catheter to two atmospheres pressure for about 5 minutes.

4. A method as claimed in claim 1, wherein the step of cooling the catheter while the lumen is maintained under internal fluid pressure is accomplished by cooling the catheter at room temperature for about 10 minutes.

5. A method as claimed in claim 1, wherein the step of reheating the catheter and lumen is accomplished by reheating the catheter to about 100° C. for about 10 minutes under atmospheric pressure.

6. A method as claimed in claim 1, further including an initial step, before the step of expanding the internal diameter of the catheter's lumen, of inserting the catheter into a cylinder made of a material having a high rigidity at an elevated temperature and having a predetermined inner diameter which is greater than the outer diameter of the catheter so that the degree of expansion of the catheter and its internal lumen can be controlled by the size of the inner diameter of the cylinder.

7. A method as claimed in claim 1, wherein the fiberscopic catheter further includes secondary lumens, in addition to the principle lumen which receives the optical fiber bundle, for providing various other functions within the catheter, and inserting a rod made of a material having a high rigidity at elevated temperatures and having a predetermined diameter in each of said secondary lumens to prevent such lumens from undue deformation or contraction during the subsequent expanding or reheating steps of claim 1.

8. A method as claimed in claim 2, wherein the step of cooling the catheter while the lumen is maintained under internal fluid pressure is accomplished by cooling the catheter at room temperature for about 10 minutes.

9. A method as claimed in claim 2, further including an initial step, before the step of heating the catheter and internal lumen, of inserting the catheter into a cylinder made of a material having a high rigidity at an elevated temperature and having a predetermined inner diameter which is greater than the outer diameter of the catheter so that the degree of expansion of the catheter and its internal lumen can be controlled by the size of the inner diameter of the cylinder.

10. A method as claimed in claim 2, wherein the fiberscopic catheter further includes a secondary lumen, in addition to the principle lumen which receives the optical fiber bundle, for providing various other functions within the catheter, and inserting a rod made of a material having a high rigidity at elevated temperatures and having a predetermined diameter in each of said secondary lumen(s) to prevent such lumen(s) from undue deformation or contraction during the subsequent heating or reheating steps of claim 8.

11. A method of making a fiberscopic catheter having an internal lumen for receiving an optical fiber bundle, comprising the steps of:

inserting the catheter into a cylinder made of a material having a high rigidity at an elevated temperature and having a predetermined inner diameter which is greater than the outer diameter of the catheter by a predetermined amount;

heating the catheter and internal lumen in a heating device at about 80° C. for about 5 minutes;

pressurizing the internal lumen of the catheter to about two (2) atmospheres pressure for about 5 minutes to expand the internal diameter of the lumen and outer diameter of the catheter so that the outer diameter of the catheter expands until it contacts the inner diameter of the cylinder;

cooling the catheter and lumen while under pressure to maintain the expanded diameters of the catheter and lumen;

releasing the internal fluid pressure within the lumen of the catheter and removing the catheter from the cylinder;

inserting the optical fiber bundle into the lumen of the catheter to a predetermined position within the catheter;

reheating the catheter and lumen to about 100° C. for about 10 minutes to contract the internal diameter of the lumen about the optical fiber bundle to provide a fiberscopic catheter having a tightly fitted fiber optic bundle.

12. A method as claimed in claim 11, wherein the fiberscopic catheter further includes at least one secondary lumen, in addition to the lumen receiving the optical fiber bundle, for providing various alternate functions within the catheter, and inserting a rod made of a material having a high rigidity at elevated temperatures and having a predetermined diameter in each of said secondary lumen(s) to prevent such lumen(s) from undue deformation during the subsequent heating and reheating steps of claim 12.

* * * * *